Figure 1:
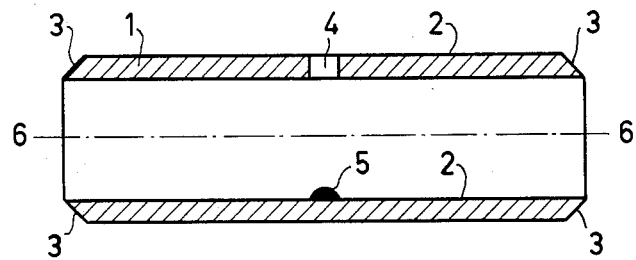

United States Patent [19]

Lersmacher et al.

[11] Patent Number: 4,629,320
[45] Date of Patent: Dec. 16, 1986

[54] CUVETTE FOR THE ATOMIC ABSORPTION SPECTROMETRY

[75] Inventors: Bernhard Lersmacher, Aachen, Fed. Rep. of Germany; Wilhelmus F. Knippenberg, Eindhoven, Netherlands

[73] Assignee: U.S. Philips Corporation, New York, N.Y.

[21] Appl. No.: 473,380

[22] Filed: Mar. 8, 1983

[30] Foreign Application Priority Data

Mar. 8, 1982 [DE] Fed. Rep. of Germany ....... 3208247

[51] Int. Cl.$^4$ ............................................. G01N 21/03
[52] U.S. Cl. ..................................... 356/244; 356/312
[58] Field of Search ................................ 356/244, 312

[56] References Cited

U.S. PATENT DOCUMENTS 3,979,162 9/1976 George .................................. 356/312

Primary Examiner—F. L. Evans

[57] ABSTRACT

A cuvette consisting of a basic hollow member of pyrolytic graphite which is treated at least on the outside surface by a local mechanical abrasion is provided for use in atomic absorption spectroscopy. Since the mechanically treated surfaces may form the inner and outer surfaces of the cuvette, it has been found that the cuvette need not be after-coated or sealed with pyrolytic graphite, but may be of a finally finished form following this mechanical abrasion. Accordingly, cuvettes of substantially smaller wall thicknesses, and substantially smaller mass, are formed with the same or even increased rigidity than commercially available graphite cuvettes which may have or not have a pyrolytic graphite coating.

5 Claims, 2 Drawing Figures

CUVETTE FOR THE ATOMIC ABSORPTION SPECTROMETRY

The invention relates to a cuvette for the atomic absorption spectrometry (AAS) which consists of a hollow basic member of pyrolytic graphite having the outside and/or the inside at least locally mechanical abraded.

The function of a cuvette for AAS, in particular for flameless AAS, i.e. for AAS with electrothermal excitation, methods of manufacturing them and the materials used therein, are known. In particular, the outstanding importance of well oriented pyrolytic graphite both as a protective layer on a basic member of a different material, for example electrographite, and as a base material for the cuvette, is known. In this connection is mentioned in particular the DE-OS No. 29 49 275. The method described in this reference has substantially for its object an advantageous combination of pyrolytic graphite as a basic member of a cuvette, and simultaneously as a protective layer on the same member. In this combination the basic member is subjected to a mechanical treatment, mainly grinding, cutting and drilling, prior to providing the protective layer, so as to give it the described shape and dimensions. Processing methods other than those mentioned, for example, laser-cutting and drilling, spark erosion and ultrasonic treatment, may also be used for the manufacture of certain shapes and dimensions. In particular the grinding process is the appropriate treatment method when a certain wall thickness of the cuvette with narrow wall thickness tolerances is to be realized. Although a prescribed wall thickness can in principle be achieved directly by a suitable choice of the deposition parameters, for example pressure, temperature and time, in practice where a large number of cuvettes are to be manufactured simultaneously in a rather large reactor, this cannot be realized since in this case depositions of different thicknesses or wall thicknesses are formed in the reactor dependent on the place of the substrate in the reactor. The grinding process may occur both from the outside and from the inside. It is generally facilitated in that in the AAS cuvette it relates in most of the cases to cylindrically symmetrical, and at least rotationally-symmetrical tubular bodies. All the treatments have for their result that the "naturally grown" surfaces of the pyrolytic graphite deposited from the gaseous phase are damaged, that is to say that as a result of the treatment a large number of reactive centers are produced on the chemically comparatively inert surfaces (in particular on the base surfaces (0002)), so that generally the chemical interaction of the cuvette surfaces with other substances is intensified. This "activation effect" is in a certain aspect advantageous for the analysis method when a reduction of the probe usually present as an oxide is associated therewith. Generally, however, it means a reduction of the life or of the re-usability of the cuvette. The examinations performed in this respect lead to the conception of a cuvette with "passivated" surface as it is described as a special type of cuvette in the DE-OS No. 29 49 275. A characteristic feature of the method as described therein is that the increase of the chemical reactivity on the cuvette surface caused by the treatment as well as the interlaminar cracks and cutting edges and drilling holes resulting from the tool pressure and operating forces, respectively, is blocked and sealed, respectively, by providing at least one further layer of pyrolytic graphite on the basic member (of pyrographite). The method according to DE-OS No. 29 49 275 leads to a AAS cuvette which in addition to the purposes determined by the exclusive use of pyrolytic graphite is characterized by a particularly long life. Earlier investigations into the chemical reactivity of the graphite surface had led to a conception of an AAS cuvette described in DE-OS No. 30 04 812 in which by various measures a directed increase of the reactivity was produced. These measures were as follows:

(a) providing a considerably misoriented and hence chemically active carbon layer (soot) on a graphite cuvette which in turn is coated with a protective layer of pyrolytic graphite, (b) mechanically roughening the protective layer mentioned sub (a), for example, by grinding (abrasive) surface treatment with quartz sand or the like.

Both after-treatment steps according to the DE-OS No. 29 49 275 were performed on usual (commercially available) laminated graphite cuvettes, so on tubes of comparatively large wall thicknesses ($d \approx 0.8$ to 1.0 mm), and have for their only object a chemical activation in the sense of an increase of its reduction activity on analysis substance present in a compound form. Elsewhere described measures, (for example DE-AS No. 23 23 774, DE-OS No. 25 54 950, U.S. Pat. No. 4,111,563) of "roughening" in the form of incorporated macroscopic notches or grooves in the cuvette body itself or in an additional insert on the contrary have for their object to concentrate as long as possible the probe to be analysed as much as possible in a given place (for example, that of the highest temperature), so to compensate for the wetting tendency of the graphite tube by the probe at least partly. In one other case (DE OS No. 25 58 948) the mechanical roughening of the outer cuvette surface serves to "preserve" the emission coefficient for thermal radiation for purposes of more exact temperature measurements.

It is the object of the invention to provide an AAS cuvette of pyrolytic graphite which with the same or even better rigidity (axial compression pressure) has substantially smaller wall thicknesses and hence substantially smaller mass than commercially available graphite cuvettes with or without pyrographite coating.

According to the invention this object is achieved by a cuvette of the kind mentioned in the opening paragraph in which the treated surfaces form the outer and inner surfaces, respectively, of the cuvette.

The hollow basic member of the cuvette is preferably a cylindrical tube. The wall thickness of the basic member is preferably 50 $\mu$m to 1000 $\mu$m, and in particular 100 $\mu$m to 300 $\mu$m.

As a matter of fact, experiments for testing known cuvette types have led to the unexpected result that in many cases it is very advantageous for analytic determinations according to the AAS method, to use cuvettes of pyrolytic graphite in the condition in which they are received after the above-described shaping treatment and a subsequent cleaning without any additional sealing by a final coating. Particularly surprising was the fact that such cuvettes can be manufactured and used with sufficient rigidity (with respect to the contacting pressure) with unusually small wall thicknesses and have a life which is entirely sufficient for most requirements. These unexpected establishments may serve as an explanation for the fact that in the literature in question no references are to be found for AAS cuvettes of this type. The considered (and measured) preferences of non-sealed pyrographite cuvettes of the kind according to the invention can be described substantially according to three characteristic features:

1. Chemical reactivity.

In general they have an increased reactivity (higher reduction potential) than sealed pyrographite cuvettes, which works out particularly favourably on the decomposition of compounds (for example oxides) in the course of the analysis. In this connection the surprising observation was also made that already with non-treated cuvettes of pyrolytic graphite a small increase of the reactivity can be established as compared with cuvettes "passivated" by subsequent coating. This effect can be explained as follows: The inner face (inner surface) "is formed" when the cuvette crude body is pulled off from the substrate for use in the pyrographite deposition. This "inner" face near to the substrate has a slightly higher degree of disorder dependent on the structure than the "naturally" grown outer surface and consequently a slightly higher reactivity than the latter. This could be proved, unambiguously, for example, in oxidation experiments by the detection of higher oxidation rates. Otherwise the reactivity of a surface roughened by mechanical or chemical aftertreatments is more pronounced.

2. Thermally inert mass and mechanical rigidity.

It was found that the AAS cuvettes according to the invention of shaped, non after-coated or sealed pyrolytic graphite at the same or even higher rigidity (axial compression pressure) can be manufactured with essentially smaller wall thicknesses and hence also substantially smaller mass than commercial graphite cuvettes with or without a pyrographite coating. This means that with the same amount of energy—with otherwise comparable dimensions of length and diameter i.e. in particular with comparable freely reflecting outer surface—partly considerably higher heating rates can be achieved. High heating rates are of great importance for the reliability and accuracy of the analysis result. As compared with cuvettes of conventional materials (for example electrographite) a homogeneous temperature distribution moreover very rapidly adjusts in cuvettes consisting only of pyrolytic graphite as a result of the excellent thermal conductivity both in the axial direction and also in the tangential (azimuthal) direction.

A particularly effective type of heating is the inductive heating of pyrographite cuvettes by means of intermediate frequency or high frequency energy, because (a) the energy supply occurs without contact, and losses by thermal dissipation by the normally used, usually cooled contacts, do not occur, (b) a homogeneous and constant temperature distribution adjusts substantially over the entire length of the cuvette. There are substantially no "cold" cuvette ends on which analysis substance could condense and thus could deteriorate the result of subsequent analyses, (c) the thermally inert mass and hence the heating rates could be optimized by mutual adaptation of the wall thicknesses of the cuvettes to the operating frequency while taking the skin effect into account.

(d) in contrast with (conventional) resistive heating (Joulean heat), technically more advantageous ratios of current and voltage (lower currents at higher voltages) can be realised and hence, for example, heavy transformers for high heating currents may be omitted.

Remark:

Since in the case of inductive, contact-free heating no mechanical forces (compression in the axial direction) influence the cuvette, the question of a suitable wall thickness and hence of a high heating rate substantially depends only on the preparatory possibilities and an expected minimum life. AAS-cuvettes of normal dimensions ($l \approx 20$ to 30 mm, $d \approx 5$ to 10 mm) could be manufactured with wall thicknesses $< 100$ $\mu$m.

3. Efficiency and costs.

As has appeared from numerous experiments performed so far the AAS-cuvettes described above are superior to the conventional cuvettes of electrographite. This applies first of all to the typical analytical characteristics: "sensitivity, heating rate, no memory effect, life-time, uniformity of temperature distribution". When in addition the cost of manufacture, in particular that for cuvettes of simple cylindrical symmetry, are compared with that for spectrally pure electrographite cuvettes, in particular for those with an additional protective layer of pyrolytic graphite, the so far performed cost estimations have demonstrated that the cost of manufacture for pure pyrographite cuvettes is by no means higher. In this connection the establishment made in the DE-AS No. 23 23 774 that the cost of pyrographite cuvettes is "unbearable" generally does not apply.

The invention will be described in greater detail with reference to a drawing and an example. In the drawing FIG. 1 is a sectional view of an AAS cuvette for horizontal operation, and FIG. 2 is a graphic representation of the heating rate of various AAS cuvettes.

Figure 2:
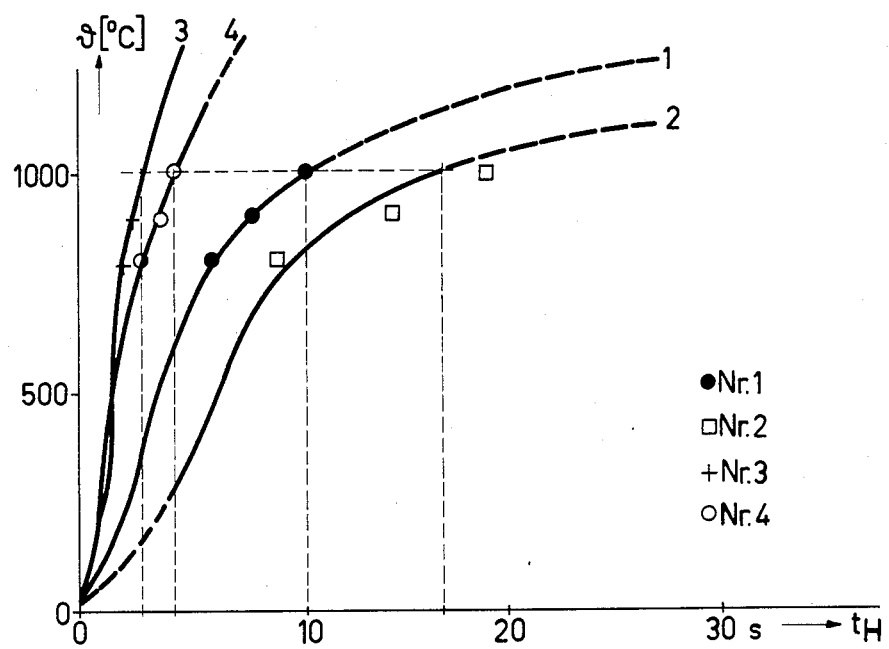

The cuvette shown in FIG. 1 consists of a basic member 1 of pyrolytic graphite whose outer and inner surfaces 2 are worked by mechanical abrasion. The cuvette has contact faces 3 at its ends. An aperture 4 provided in the wall of the cuvette serves to provide the cuvette with analysis material 5. The measuring ray during operation passes through the cuvette along the line 6—6.

EXAMPLE manufacture of cuvettes 5.4/5.5 mm$\phi \times$28 mm length.

(a) Deposition.

250 cylindrical rods of electrographite of approximately 75 mm length and 5 mm diameter were arranged in a hot wall reactor (on supporting plates of graphite in 4 storeys). After evacuating the reactor vessel to $p = 10^{-3}$ mbar and heating the reactor chamber to 2100° C. (within 2 hours) a low molecular hydrocarbon gas (propane $C_3H_8$) was admitted in the reactor chamber. The inflowing quantity of gas and the draining pipes of the connected pump system were controlled so that an overall pressure of 2.4 to 2.5 mbar was adjusted in the reactor below flowing gas. After 30 hours the gas supply was cut off and the system was cooled in a vacuum. After cooling, the substrate rods were removed. They were covered with a layer of pyrolytic graphite which in accordance with the position in the reactor had a thickness between 250 $\mu$m and 500 $\mu$m—corresponding to an increase in diameter of at least 0.5 mm and 1.0 mm. The pyrographite layer enveloping the substrates was then pulled off from the substrate core and was thus available as approximately 70 mm long pyrographite tubes of approximately 5.0 mm inside diameter and 5.5 to 6.0 mm outside diameter. These tubes were provided for further processing as crude bodies for cuvettes.

(b) Treatment.

From the crude bodies mentioned sub (a) first 28.0 mm long tubes were cut by means of a separating disc. These tubes were then ground down to a uniform wall thickness of 200 μm on a circular grinding machine by means of diamonds-equipped grinding discs and, by using a drilling jig, were then provided with the filling aperture in the center of the tube wall.

After treatment the finished AAS-cuvettes were subjected to a cleaning in several steps
  (a) cleaning in a freon-filled ultrasonic bath with final cleaning in freon vapour
  (b) annealing in a vacuum ($p<10^{-4}$ mbar) at $\upsilon=1800°$ C. for one hour.
  (c) General properties.

The AAS cuvettes of pyrolytic graphite manufactured and after-treated according to (a) and (b) had on an average a mass of approximately 0.15 g. During the measurement a change in the inside diameter of approximately 0.1 mm occurred dependent on the thermal expansion of the substrate core upon heating to the deposition temperature (2000° C. to 2100° C.) so the actual wall thickness was on an average of 150 μm. This corresponds to a volume of the cuvette body of approximately 0.0693 cm$^3$ or an average specific weight of $\gamma=2.165$ gcm$^{-3}$ which was confirmed by numerous pycnometric measurements. The rigidity against axial compression pressure was on an average $\sigma_k=3.2$ kpmm$^{-2}$ which corresponds to a contact force (or rigidity) up to $P_k\approx 8$ kg.
  (d) Heating rate.

A few comparative experiments were carried out in which bodies of graphite and pyrographite, respectively, were heated in a high-frequency electromagnetic field (f=630 kHz) of a nominal capacity which was kept constant. Each time the time was measured (in s) which was necessary to reach the temperatures $\upsilon=800°$ C., 900° C. and 1000° C. after switching on the HF generator (t=0). From these experiments 4 probes were selected which all had the same length (l=28 mm) and differed from each other only in material and in the diameters as well as the masses. In detail it concerns the probes
  No. 1 Commercially available AAS-cuvette of electrographite with pyrographite protective layer, outside diameter 8.1 mm, inside diameter 6.2 mm, mass 0.960 g.
  No. 2 Graphite tube of the same outside diameter as No. 1 but without pyrographite layer, mass 0.591 g.
  No. 3 Pyrographite tube, outside diameter 7.5 mm, inside diameter 7.2 mm, mass 0.256 g.
  No. 4 Pyrographite cuvette, according to Example with 5.4 mm outside diameter, mass 0.153 g.

The results are recorded in FIG. 2 by comparative equilibrium curves and demonstrate that the pyrolytic graphite is the material component decisive of the heating rate. The more rapid increase in temperature of probe No. 3 as compared with No. 4 can be explained in that as a result of a slightly larger outside diameter the adaptation to the preset electromagnetic field is somewhat more favourable. It is to be noted that with optimum field adaptation ($d_{probe}/d_{coil}$) and doping of the HF power even more rapid rises in temperature can be achieved.

What is claimed is:

1. In a cuvette for atomic absorption spectroscopy comprising a basic hollow member of pyrolytic graphite, wherein said member has been treated at least exteriorly by a local mechanical abrasion, the improvement comprising a final cuvette consisting of said treated member.

2. A cuvette according to claim 1, wherein both exterior and interior surfaces of said cuvette are treated by said mechanical abrasion.

3. A cuvette according to claim 1, wherein said basic hollow member is a tubular cylinder.

4. A cuvette according to claim 1, wherein said basic member has a wall thickness of 50 micron to 1000 micron.

5. A cuvette according to claim 4, wherein said wall thickness is 100 micron to 300 micron.

* * * * *

UNITED STATES PATENT AND TRADEMARK OFFICE
CERTIFICATE OF CORRECTION

PATENT NO. : 4,629,320

DATED : December 16, 1986

INVENTOR(S) : Bernhard Lersmacher ET AL

It is certified that error appears in the above-identified patent and that said Letters Patent is hereby corrected as shown below:

Column 2, line 16, after "mentioned" insert --in--

Column 4, lines 40-43; change

"EXAMPLE
manufacture of cuvettes 5.4/5.5 mm∅ x 28mm length"
to
 --EXAMPLE: manufacture of cuvettes 5.4/5.5 mm ∅ x 28mm in length--

Signed and Sealed this

Seventeenth Day of November, 1987

*Attest:*

*Attesting Officer*

DONALD J. QUIGG

*Commissioner of Patents and Trademarks*